April 20, 1976
M. R. RIEGER
BEGONIA PLANT
Filed Jan. 24, 1975
Plant Pat. 3,868
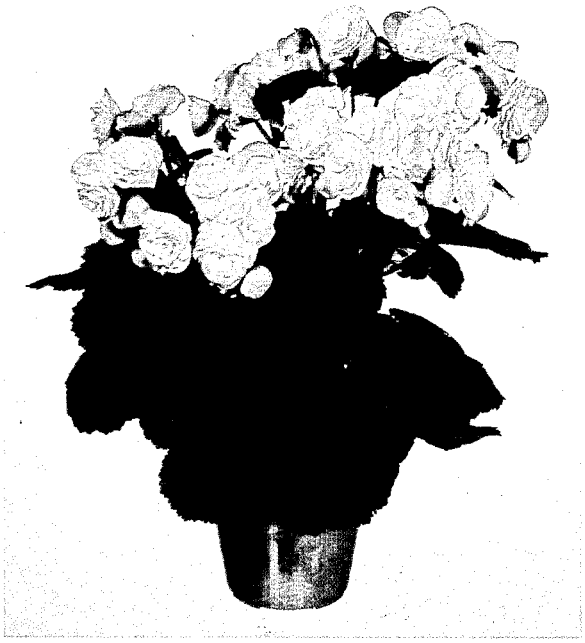

United States Patent

Plant Pat. 3,868
Patented Apr. 20, 1976

3,868

BEGONIA PLANT

Margarete Rohde-Rieger, Nurtingen, Germany, assignor to Mikkelsens, Inc., Ashtabula, Ohio Filed Jan. 24, 1975, Ser. No. 543,911
Int. Cl. A01h *5/00*
U.S. Cl. Plt.—68 1 Claim The present invention relates to a new and distinctive cultivar of begonia plant, botanically known as *Begonia elatior* (*hiemalis*-Fotsch), and known by the cultivator name Ballerina.

The new cultivar was discovered by me in a group of new begonia plants from hybridized seed in a controlled breeding program. The seed parent is an unnamed, unpatented *Begonia tuberhybrida* and the pollen parent is an unnamed unpatented *Begonia socotrana.* Asexual reproduction by stem and leaf cuttings has reproduced the unique features of the new cultivar through successive propagations.

The following characteristics when combinead distinguish the new begonia from other begonias commercially known and used in the floriculture industry:

1. Apricot-orange color of flowers. Upon maturing the flowers gradually turn to a yellow-orange color. This variation of color on the same plant adds considerable interest for the ultimate consumer.

2. Flowers are double with odd numbers of tepals, varying in number more or less from 21 to 31.

3. The new cultivar is very fast growing and requires growth regulators for height control when produced under high light and temperature environment.

4. General plant characteristics somewhat resemble the Rieger Aphrodite types, but better stem vigor allows this new cultivator to be better adapted to upright growth. Reference is made to U.S. Letters Plant Patent No. 3,318 (Aphrodite Pink) and U.S. Letters Plant Patent No. 3,319 (Aphrodite Cherry Red).

5. The new cultivar is highly resistant, if not immune, to common, powdery mildew.

6. Individual flowers are extremely long lasting (up to two months) which is of great value to the producer by allowing a wide spread selling period. Ballerina is one of the most long lasting flowering begonias developed to date.

7. Applications of cycocel intensifies the flower color toward orange-red.

8. When cultivar is placed outside in summer in the area of Nurtingen, Germany, the flowers fade to deep golden yellow. Normally, flower color intensifies rather than fades during outdoor flowering conditions.

The accompanying colored photographic drawing taken in Nurtingen, Germany illustrates the overall appearance of the new cultivar taken as a face view of the plant. The photograph shows the colors as true as it is reasonably possible to obtain in a colored reproduction of this type.

The following is a detailed description of my new begonia variety based on plants produced under commercial practices in Nurtingen, Germany. Color references are made to the Royal Horticultural Society Colour Chart except where general color terms of ordinary dictionary significance are used.

Parentage: The new cultivar is the result of controlled pollination of a selected *Begonia tuberhybrida* as the seed parent crossed with *Begonia socotrana* as the pollen parent.

Propagation: Propagation is very rapid by leaf cuttings, being two weeks faster than Schwabenland, disclosed in U.S. Letters Plant Patent No. 3,320, granted Mar. 13, 1973 to Otto Rieger, deceased. Initiation and development of 3–6 adventitious buds is very consistant at all times of the year and especially good in summer months when the Schwabenland types are inconsistent. Stem cuttings may also be used for propagation as there is considerable self-branching.

Rooting habits: Very easy to root at 20°–22° C. Roots are abundant, fibrous, and have a dendritic pattern.

Plant form: Bascially upright, tending to be vining under high light environments.

Habit of growth: Very free growing.

Blooming habits: After flower initiation, there is profuse blooming over a long period of time.

Blooming season: Natural flowering season is in November in Germany. By use of controlled environments of temperature and daylight Ballerina can be commercially produced anytime.

Foliage: Near average for this type of begonia.

Size: 15 cm. across by 12 cm. long. Leaf size will vary with growing conditions.

Shape: Nearly round.

Texture: Leathery.

Margin: Nearly complete with few serrations or sinus indentations. Young leaves are sharply serrated.

Color:

*Young leaves.*—Upper side, darker than 147A green. Lower side, green mixed with red.

*Mature leaves.*—Upper side, darker than 139A green. Lower side, 147C yellow green.

Disease resistance: More resistant to powdery mildew than the Schwabenland types but somewhat less resisttant than the Aphrodite types when all are tested under conditions for optimum mildew growth.

Flowers:

*Borne.*—On strong upright peduncles. Flowers are double with average of 25 tepals. Odd numbers of tepals usually occur. Edges of flowers are sometimes very wavy.

*Quantity.*—Average for elatior type begonias. Long lasting double flowers and variable color tones give an appearance of greater flowering.

*Buds.*—Flat, measuring 25 mm. in diameter before flowering.

*Tepals.*—Total flower size 45 mm. to 60 mm. in diameter.

*Color.*—The flower color is very difficult to give a value for due to the above noted changes in flower color during maturation. When the flowers open in the greenhouse, the upper side of the tepals range from orange-red 32B to orange 29B, and the underside of the tepals red 39B to 39C. As the tepals mature there is a fading of the color toward a yellow-orange, for example 23C, although the faded color is not consistent. The underside color does not fade appreciably. A further complicating factor in color value determination is that in outdoor flowering, the flower color tends to fade rather than intensify which is normally the case.

I claim:

1. A new and distinct cultivar of begonia plant characterized particularly as to uniqueness by its apricot-orange flower color which gradually fades to yellow-orange; double flowers with odd number of tepals; very fast growing habit which requires growth regulation for height control in high light and high temperature conditions; long lasting individual flowers which last up to two months, and by its tendency to fade in flower color under outdoor flowering conditions.

No references cited.

ROBERT E. BAGWILL, Primary Examiner